(12) United States Patent
Lass, Jr. et al.

(10) Patent No.: US 9,168,774 B2
(45) Date of Patent: Oct. 27, 2015

(54) TRI-STATE DETECTOR FOR DETECTING TYPES OF LIGHT

(71) Applicant: ZIH Corp., Lincolnshire, IL (US)

(72) Inventors: Robert Edward Lass, Jr., Long Grove, IL (US); Robert A. Ehrhardt, Jr., Palatine, IL (US)

(73) Assignee: ZIH Corp., Lincolnshire, IL (US)

( * ) Notice: Subject to any disclaimer, the term of this patent is extended or adjusted under 35 U.S.C. 154(b) by 369 days.

(21) Appl. No.: 13/735,334

(22) Filed: Jan. 7, 2013

(65) Prior Publication Data

US 2013/0177343 A1  Jul. 11, 2013

Related U.S. Application Data

(60) Provisional application No. 61/584,061, filed on Jan. 6, 2012.

(51) Int. Cl.
*G01N 21/86* (2006.01)
*B41J 31/14* (2006.01)
*B41J 17/36* (2006.01)
*B41J 35/18* (2006.01)

(52) U.S. Cl.
CPC *B41J 31/14* (2013.01); *B41J 17/36* (2013.01); *B41J 35/18* (2013.01)

(58) Field of Classification Search
CPC ............. B41J 17/36; B41J 31/14; B41J 35/18
USPC ..................................................... 250/559.09
See application file for complete search history.

(56) References Cited

U.S. PATENT DOCUMENTS

| | | | | |
|---|---|---|---|---|
| 4,224,608 | A | * | 9/1980 | Lederer ......................... 340/556 |
| 5,844,682 | A | * | 12/1998 | Kiyomoto et al. ......... 356/237.1 |
| 8,878,652 | B2 | | 11/2014 | Tsirline et al. |
| 2008/0088818 | A1 | * | 4/2008 | Mori .............................. 356/5.1 |

* cited by examiner

*Primary Examiner* — Thanh Luu
(74) *Attorney, Agent, or Firm* — Alston & Bird LLP

(57) ABSTRACT

Provided herein are devices, systems, methods and various means, including those related to printer systems and, more particularly, relate to methods, apparatuses, systems and other means for monitoring a printer ribbon. Some embodiments use a multi-element detector, which is configured to detect a particular type of light emitted from a light emitter. The multi-state detector can include two sensors, one of which includes a polarizer filter that blocks polarized light. Embodiments can be used to determine, among other things, whether or not a printer ribbon is installed in a printer without the use of a snap plate.

16 Claims, 9 Drawing Sheets

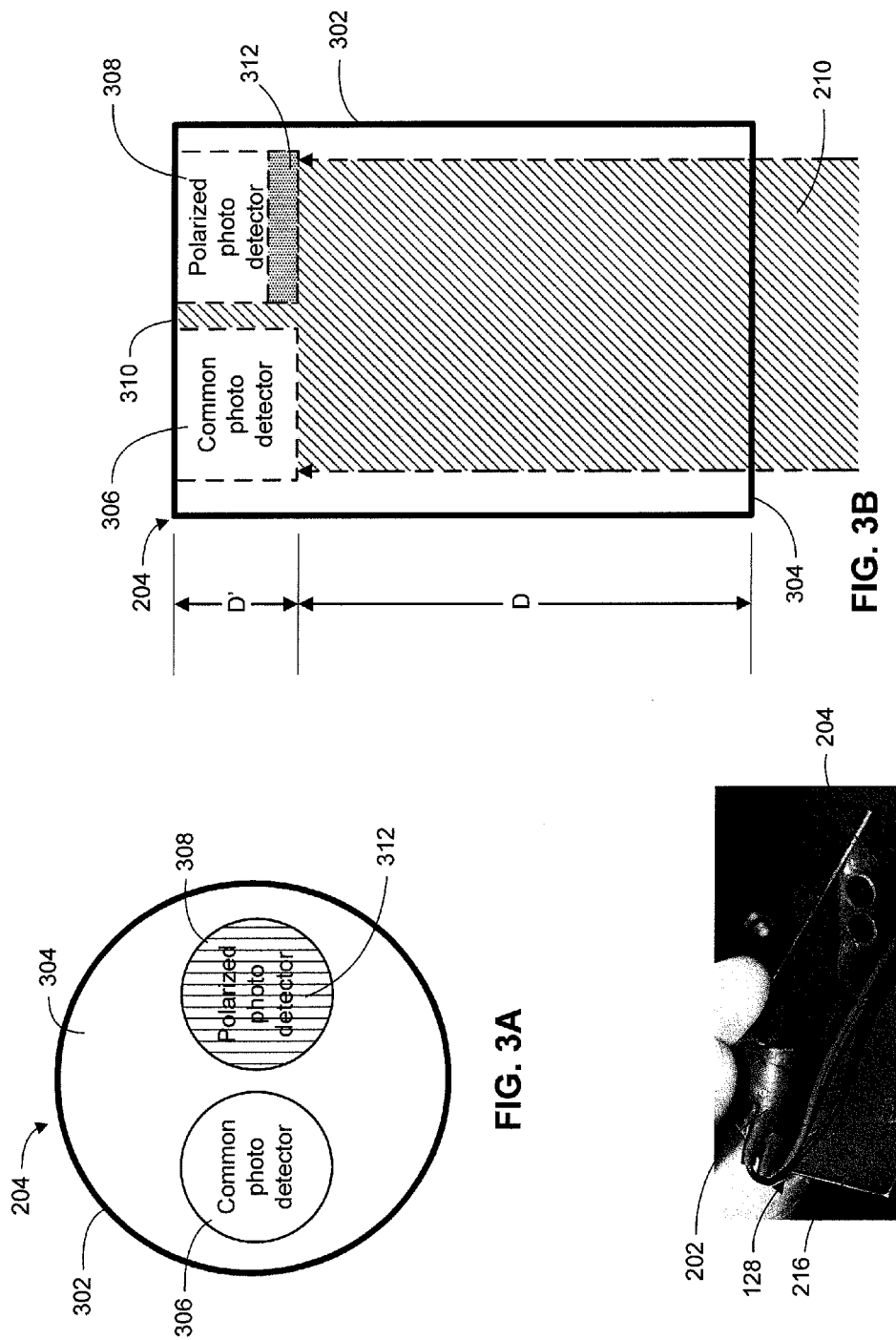

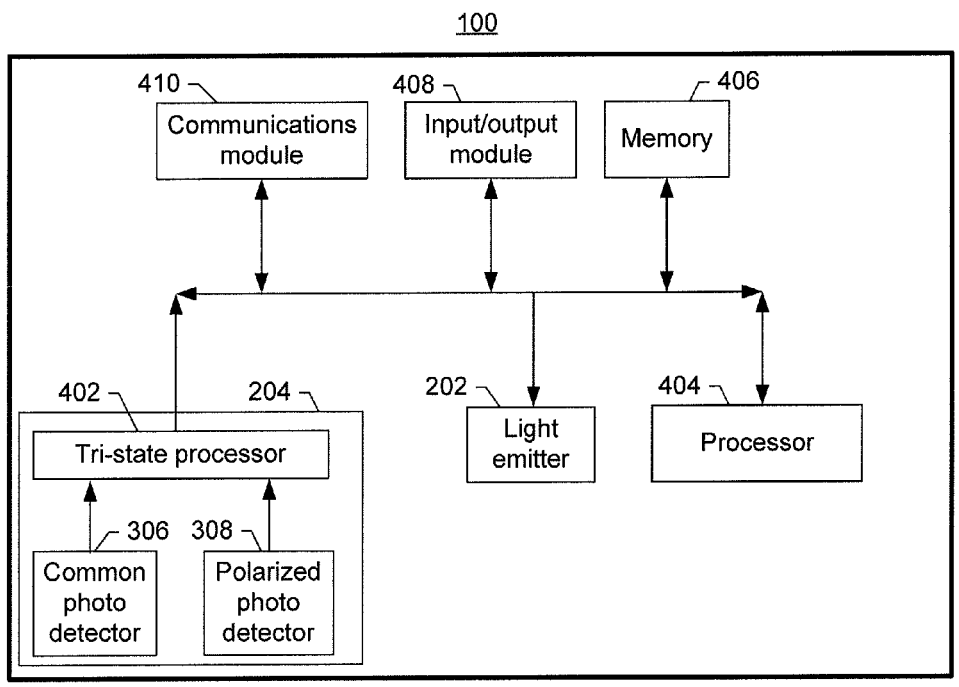

FIG. 4

| Common photo detector | Polarized photo detector | Config. of FIG. 2A looking for non-reflective inked ribbon, reflective trailer | Config. of FIG. 2b looking for reflective ink, clear trailer | Config. of FIG. 2C looking for reflective inked ribbon, and/or clear trailer |
|---|---|---|---|---|
| 0 | 0 | No ribbon | No ribbon | No ribbon |
| 0 | 1 | Error | Error | Error |
| 1 | 0 | Inked ribbon | Ribbon trailer | Ribbon trailer |
| 1 | 1 | Ribbon trailer | Inked ribbon | Inked ribbon |

FIG. 5

TRI-STATE DETECTOR FOR DETECTING TYPES OF LIGHT

This application claims priority to the provisional application Ser. No. 61/584,061 filed Jan. 6, 2012, which is incorporated herein in its entirety.

FIELD

Embodiments of the present invention relate generally to printer systems and, more particularly, relate to methods, apparatuses, systems and other means for monitoring a printer ribbon.

BACKGROUND

Embodiments of the present invention are directed to printers and other systems for printing media including labels, receipt media, paper, cards, and the like. A number of deficiencies and problems associated with the manufacture, use, and maintenance of conventional printers have been identified. Through applied effort, ingenuity, and innovation, solutions to many of these identified problems have been solved by developing solutions that are included in the various embodiments of the present invention, some examples of which are detailed below.

BRIEF DESCRIPTION OF THE SEVERAL VIEWS OF THE DRAWINGS

Reference will now be made to the accompanying drawings, which are not necessarily drawn to scale, and wherein:

FIGS. 3A and 3B show various embodiments of sensors that may be used in accordance with some embodiments discussed herein;

FIG. 3C shows a component that may be configured to perform tri-state detection functionality in accordance with some embodiments discussed herein;

FIG. 4 shows a block diagram of circuitry that may be incorporated into a machine in accordance with various embodiments discussed herein;

FIG. 5 shows a logic table representing inputs and outputs of a logic algorithm that may be implemented by some embodiments discussed herein.

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 1:
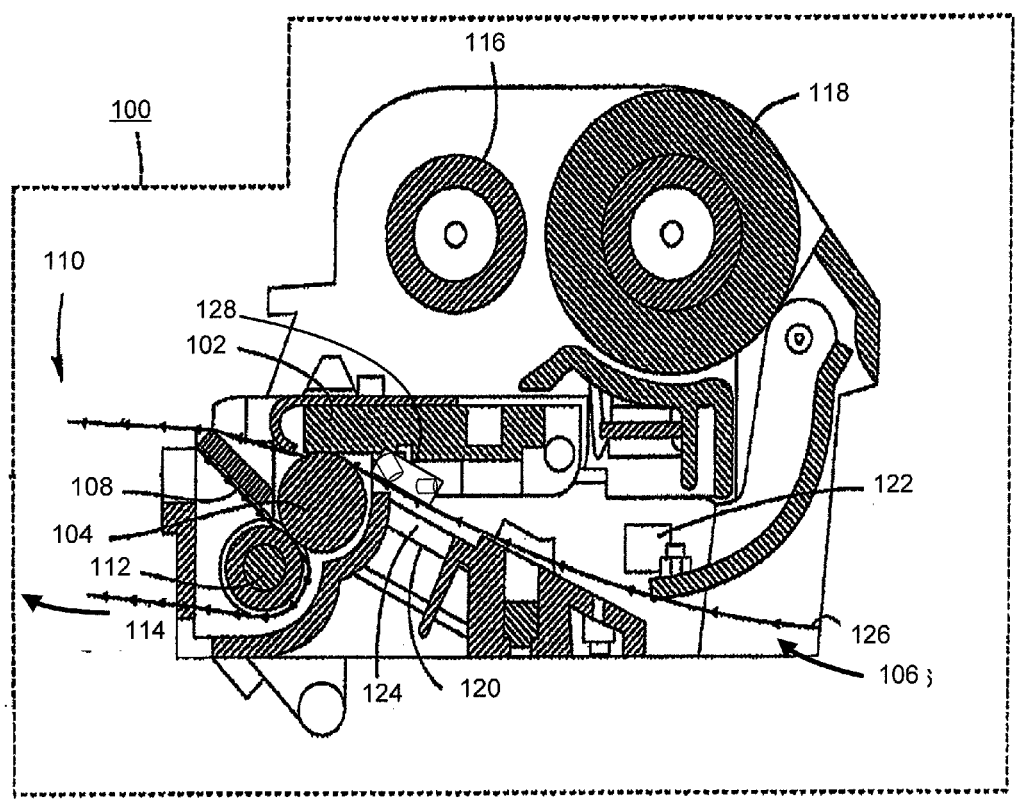
FIG. 1 shows an example system that may be configured to implement some embodiments discussed herein.

FIG. 1 shows an example system, namely printer 100 that can be configured to print indicia (using, e.g., black, colored, metallic, infrared, ultraviolet and/or any other type of ink) and/or encode data onto digital storage devices of one or more radio frequency identification ("RFID") tags. In some embodiments, for example, printer 100 may be an RFID printer-encoder configured to print and encode a series or stream of tags and/or transponders. Printer 100 comprises and defines various components and paths, including a printhead 102, a platen roller 104, a feed path 106, a peeler bar 108, a media exit path 110, rollers 112, a carrier exit path 114, a ribbon take-up spool 116, a ribbon supply roll 118, a reader 120, a controller 122, and an encoding element 124 (also sometimes referred to herein as a "coupling device").

As referred to herein, RFID tags may include labels, cards, etc., that are carried by web 126, which may be, e.g., a substrate liner. Reader 120 can be configured to generate and transmit RF communication signals that are broadcasted by encoding element 124 located proximate media feed path 106. For purposes of the present description, reader 120 and encoding element 124 may be referred to collectively as forming at least part of a communication system. In some embodiments, encoding element 124 may include, for example, an array coupler, some examples of which are discussed in commonly-assigned U.S. patent application Ser. No. 12/618,107, filed Nov. 13, 2009 and titled "Encoding Module, Associated Encoding Element, Connector, Printer-Encoder and Access Control System", which was hereby incorporated by reference in its entirety. As another example, encoding element 124 may include a single antenna coupler.

Web 126 can be directed along the feed path 106 and between the printhead 102 and the platen roller 104 for printing indicia onto one or more tags. The ribbon supply roll 118 provides a thermal ribbon (discussed below, although not shown in FIG. 1) that extends along a path such that a portion of the ribbon is positioned between the printhead 102 and the tag(s). The printhead 102 can be configured to heat up and press a portion of the ribbon onto the media to print indicia. Take-up spool 116 can be configured to receive and spool the used ribbon. This printing technique is sometimes referred to as thermal transfer printing. However, several other printing techniques may be used including, but not limited to, direct thermal printing, inkjet printing, dye sublimation printing, and/or dot matrix printing, among others.

Most references to the material represented by the web 126 in this description will be to a ribbon, often an "inked" ribbon for printing on paper or an item. It shall be understood that the material 126 passing through the printer may also take one of several other forms, such as a continuous band of RFID tags for application to a surface, a band of labels, a sequence of cards, lamination material, and many other possible materials. Individual cards, for instance, may be subject to detection of leading or trailing edges for the purpose of "registration" so that they may be applied or aligned correctly on another surface. The "web" 126 therefore is to be understood as a continuous sequence of some material passing through the mechanism subject to detection as described below.

Additionally, in accordance with some embodiments, printer 100 can include tri-state sensor 128. Tri-state sensor 128 may be configured to use light to determine (1) the presence of a ribbon trailer/leader portion of a thermal ribbon, (2) the presence of an inked portion of a thermal ribbon, or (3) the absence of any thermal ribbon (or web of material as described above). Furthermore, unlike some existing systems that may have difficulty determining the presence of ribbon having some colors of ink thereon, embodiments of tri-state sensor 128 can be configured to detect printer ribbon having ink thereon regardless of the color and/or density of the ink on the ribbon.

Tri-state sensor 128 may be used instead of or in addition to other systems and methods of determining whether or not a printer ribbon is present. For example, tri-state sensor 128 may be used in conjunction with or instead of transmissive ribbon sensing that relies on the optical density of the printer ribbon to block the light path and a reflective "snap plate" or a reflective ribbon trailer that reflects light signalling that there is a "ribbon out" condition. While there are a number of advantages of transmissive ribbon sensing, it can be less reliable than the tri-state sensor 128 (discussed herein) at identifying the presence of clear or colored ribbons with ink having low optical density. Furthermore, the presence of the snap plate can sometimes impede the ease of use of the system, because the installed snap plate can cause the loading to be more complicated for a user and the printing more prone to media jams, as compared to using tri-state sensor 128. Because of erroneous ribbon out indications, some users may choose to simply not install the snap plate, which compromises ribbon sensing. Tri-state sensor 128, on the other hand, can operate exclusively from a single side of the ribbon, can accommodate a wide flutter gap, and can totally eliminate the need for a snap plate or any other opposing reflector.

Figure 2A:
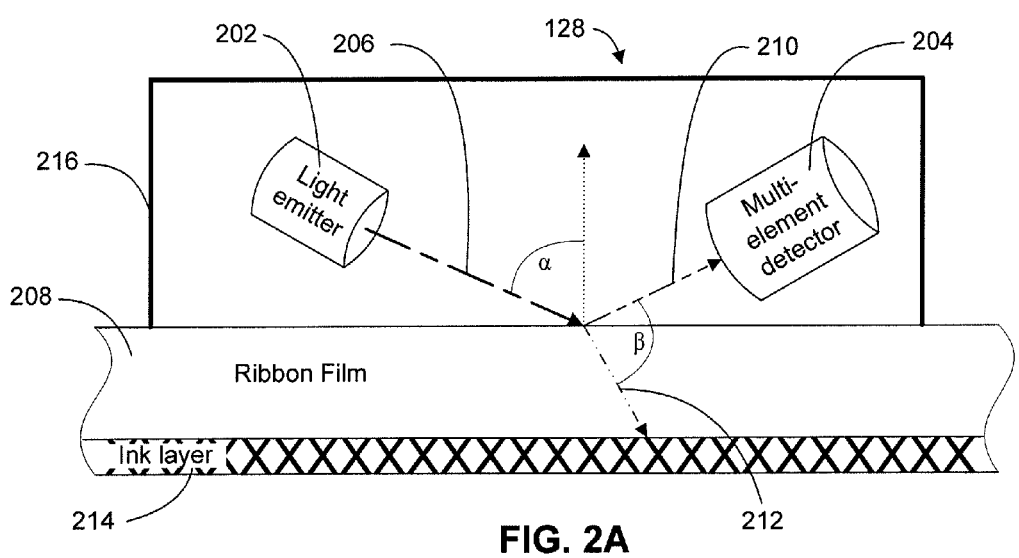
FIGS. 2A, 2B and 2C show example components that may be configured to perform tri-state detection functionality in accordance with some embodiments discussed herein.
Figure 2B:
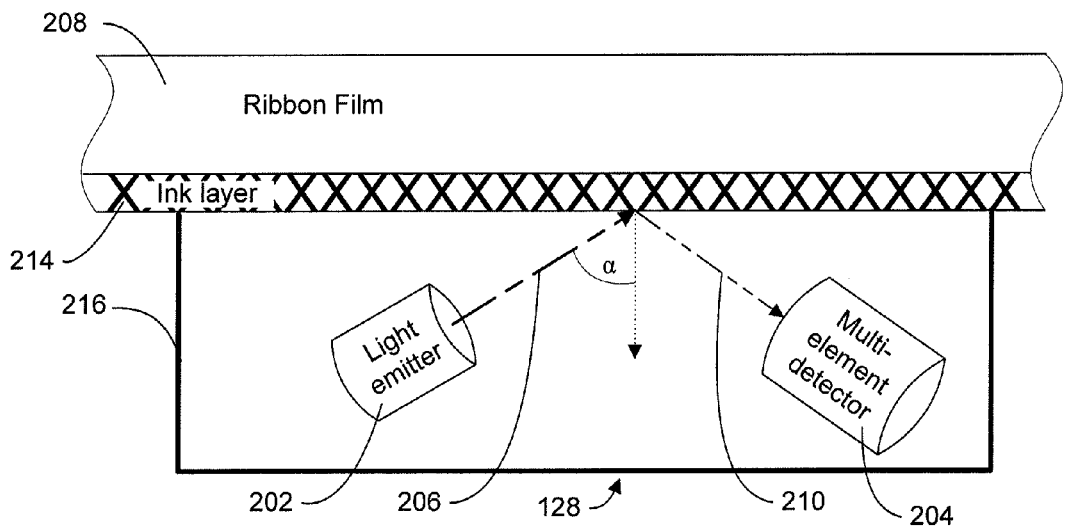
Figure 2C:
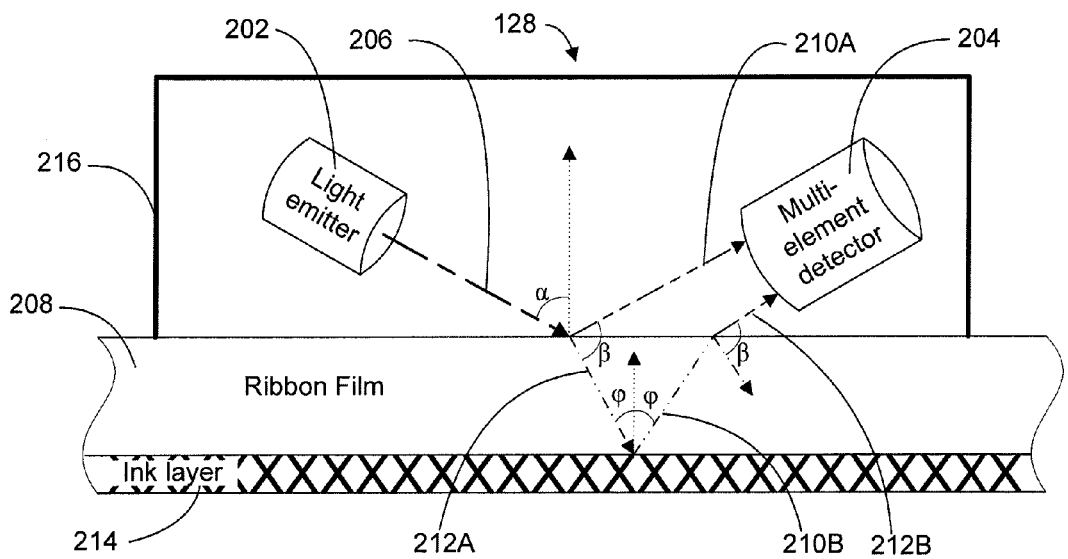

More detailed examples of tri-state sensor 128 are shown in FIGS. 2A, 2B and 2C. Tri-state sensor 128 may include light emitter 202 and multi-element detector 204. Light emitter 202 can be any suitable light source, including a laser light source, incandescent light source, fluorescent light source, ultraviolet light source, infrared light source, and/or any other type of light source. Light emitter 202 can be configured to receive a command from circuitry, such as a printer's processor (examples of which are discussed in connection with FIG. 4), and in response emit light beam 206. Each command can cause light emitter 202 to emit light beam 206 as a constant beam of light (that is, e.g., present so long as the command, such as a logical high signal, is received by light emitter 202), a pulsed light beam, and/or any other type of light beam. Light beam 206 can also include any suitable wavelength(s) of light, and may comprise an un-polarized and randomly polarized beam of light.

Light emitter 202 can be configured to direct a light beam 206 at the surface of ribbon film 208, such that the light beam 206 has an angle of incidence, "$\alpha$". The angle $\alpha$ can be configured by adjustment of the light emitter 202 to be the Brewster's angle, also known to those skilled in the art as the "polarized angle," associated with the material that comprises ribbon film 208. Ribbon film 208 may be comprised of any suitable transparent dielectric material. For example, ribbon film 208 may be made of polyethylene terephthalate ("PET"), which has a Brewster's angle of about 59 degrees at its interface with air. One skilled in the art would appreciate that some embodiments may be configured to have other Brewster's angles when materials other than PET and/or air (such as glass, plastic, quartz, liquid(s) at room temperature, other gas(s), etc.) are used. As such, light emitter 202 can be configured to direct light beam 206 at ribbon film 208, such that angle $\alpha$ is the Brewster's angle (plus or minus, e.g., 5 degrees) associated with the materials' interface (e.g., PET and air interface) being crossed by the direct light beam 206. When direct light beam 206 impacts the interface of the materials at the Brewster's angle, reflected light beam 210 can be polarized after reflecting off ribbon film 208. Some light, shown as refracted light beam 212, will also be refracted into ribbon film 208 at an angle "$\beta$", which may be 90 degrees, relative to reflected light beam 210.

Multi-element detector 204 can be configured to receive reflected light beam 210. As shown in FIG. 2A, ink layer 214 may comprise low optical density and/or absorptive inks that may not affect the trajectory and/or properties (e.g., polarized, un-polarized, etc.) of reflected light beam 210. In other embodiments, such as those discussed in connection with FIGS. 2B and 2C, the color, composition, density and/or other properties of ink layer 214 may alter the output of multi-element detector 204. As such, the properties of ink layer 214 can have varying degrees of relevance to different embodiments of tri-state sensor 128 that are discussed herein.

For example, in embodiments such as that shown in FIG. 2B, tri-state sensor 128 can include light emitter 202 that is configured to shine light beam 206 onto ink layer 214, rather than ribbon film 208. In such embodiments, the properties of ink layer 214 will affect the properties of reflected light beam 210 that are received by multi-element detector 204. For example, when ink layer 214 comprises a metallic ink that is reflective, reflective light beam 210 may comprise un-polarized light.

Embodiments similar to or the same as that shown in FIG. 2B may be problematic in some instances. For example, when opaque and/or dull non-reflective ink surfaces are installed (e.g., accidently or intentionally) in printer 100 configured as shown in FIG. 2B, printer 100 may produce an erroneous "ribbon-out indication."

FIG. 2C shows another example in accordance with some embodiments of the present invention. In FIG. 2C, tri-state sensor 128 can include light emitter 202 that is configured to shine light beam 206 onto ribbon film 208, similar to that shown in FIG. 2A. Light emitter 202 can be configured to direct light beam 206 at the surface of ribbon film 208, such that light beam 206 has an angle of incidence "$\alpha$". The angle $\alpha$ can be configured to be the Brewster's angle (plus or minus, e.g., 5 degrees) associated with both the media (e.g., air) through which the light travels before arriving at ribbon film 208 and material that comprises ribbon film 208 (e.g., PET and air). When direct light beam 206 impacts the interface of the materials at the Brewster's angle, reflected light beam 210A can be polarized after reflecting off ribbon film 208. Some light, shown as refracted light beam 212A, will also be refracted into ribbon film 208 at an angle "$\beta$", which may be 90 degrees, relative to reflected light beam 210A. Refracted light beam 212B may be slightly polarized light, which may be received by the polarized detector (discussed below) and interpreted as un-polarized light, even when $\alpha$ is the Brewster's angle.

Multi-element detector 204 can be configured to receive reflected light beams 210A and 212B when ink layer 214 comprises reflective (e.g., metallic) inks. Angle "$\phi$" is the angle at which refracted light beam 212A is incident to and reflected off ink layer 214 as reflected light beam 210B. When ink layer 214 comprises reflective ink(s), reflected light beam 210B can include un-polarized light. When ink layer 214 does not include a reflective material, light beam 210B would not be present or at least be substantially reduced in intensity.

Upon reaching the boundary of ribbon film 208, at least a portion of the un-polarized light included in reflected light beam 210B can exit ribbon film 208, as refracted light beam 212B, and be detected by the components of multi-element detector 204 (discussed below). In this regard, multi-element detector 204 can be used to determine whether ink layer 214 comprises reflective ink. Some of reflected light beam 210B can be reflected back into ribbon film 208 at angle $\beta$. In other embodiments, the printer can be configured to associate the detection of a reflective material with the presence of a reflective leader/trailer (instead of with a reflective ink).

In some embodiments, when ink layer 214 is comprised of one or more low optical density and/or absorptive inks, a substantial amount (e.g., most and/or all) of refracted light beam 212A may pass through or be absorbed into ink layer 214 and, as a result, the strength of reflected light beam 210B (and any un-polarized light comprising it) can be substantially (or completely) eliminated as compared to when ink layer 214 includes one or more reflective inks. As such, light beams 210B and 212B may only exist in a detectable form when there is a reflective material located on the opposite side of ribbon film 208. In this regard, multi-element detector 204 can be configured to generate indications associated with an absence of un-polarized light (e.g., an absence of refracted light beam 212B), thereby enabling printer 100 to determine that ink layer 214 comprises a lack of a reflective surface, which may be interpreted by circuitry as the presence of non-reflective ink or the presence of a ribbon's non-reflective trailer/leader.

Additional examples of systems, methods and other means for utilizing the embodiments of FIGS. 2A, 2B and 2C are discussed further in connection with, e.g., FIGS. 5-8.

All the components of tri-state sensor 128 may be protected and/or otherwise enclosed on at least one side by enclosure 216. In some embodiments, enclosure 216 may define at least one opening that allows light beam 206 and reflected light beam 210 to be shined onto and reflected off of ribbon film 208 and/or ink layer 214. Enclosure 216 may be made of any suitable material(s) (e.g., metal, plastic, etc.) and be colored any suitable color (e.g., black).

It should also be noted that a printer or other mechanism through which a web of material passes that requires detection on its way to the processing point (e.g., print head, label applicator, etc.) may also have more than one detector monitoring the web. In addition to the detector shown in FIG. 1 (before the print head), another detector might be placed downstream of the process point (that is, after the process point or between two or more process points).

FIG. 3A shows a front view of multi-element light detector 204 and FIG. 3B shows a top view of multi-element light detector 204. Multi-element light detector 204 may include a cylindrical and/or other type of outer housing, namely housing 302. Housing 302 may define opening 304 into which reflected light beam 210 may enter. Housing 302 may also comprise any suitable materials, including metal, plastic, rubber, and/or carbon fiber, among other things. In some embodiments, housing 302 may be the color black and/or include other configurations that enable housing 302 to minimize the amount of ambient light that reaches common photo detector 306 and polarized photo detector 308. For example, housing 302 may be a black, plastic tube formed using injection molding techniques.

As another example, as shown in FIG. 3B, positioning common photo detector 306 and polarized photo detector 308 at end 310 of housing 302, which is located opposite opening 304, may also aid in minimizing the amount of ambient light and/or other type of optical noise that may otherwise be received by common photo detector 306 and/or polarized photo detector 308. The common photo detector 306 emits an electronic signal when light impinges on a photo-electric surface. The common detector reacts to broadband light and filtered or polarized light, any light that reaches it. Some photo detectors produce a signal proportional to the intensity of detected light up to a saturation level; others may quickly reach saturation, producing a nearly binary output (e.g., "0" for no light; maximum output ("1") for any significant detected light). The polarized photo detector produces an output signal when light of the correct polarization impinges on its photo-electric surface.

The distance "D," defined by the distance between opening 304 and common photo detector 306 and polarized photo detector 308, can be configured such that housing 302 can absorb at least some, if not most, of the noise that may negatively impact the performance of multi-element light detector 204 (e.g., noise that may cause multi-element light detector 204 to yield a false positive as a result of detecting ambient light as opposed to light emitted by light emitter 202).

As another example, housing 302 may be omitted from multi-state detector 204. For example, if the enclosure of tri-state sensor 128 is completely sealed and/or located in a dark area, such that ambient light cannot enter or is otherwise minimized, there may not be any need for housing 302. Rather, for example, the common photo detector 306 and/or the polarized photo detector 308 can be mounted (e.g., glued, soldered, welded, etc.), in some embodiments, directly onto the enclosure 216 and/or other component of tri-state sensor 128 as illustrated in FIG. 3C.

Regardless of how the common photo detector 306 and the polarized photo detector 308 are integrated into apparatuses in accordance with embodiments discussed herein, the distance "D'," defined by the length of the common photo detector 306 and/or the polarized photo detector 308, can further assist in absorbing at least some, if not most, of the noise that may negatively impact the performance of multi-element light detector 204 (e.g., noise that may cause multi-element light detector 204 to yield a false positive as a result of detecting ambient light as opposed to light emitted by light emitter 202). In some embodiments, D' may vary between the common photo detector 306 and the polarized photo detector 308.

Common photo detector 306 and polarized photo detector 308 can comprise any suitable sensor of light and/or other type of electromagnetic energy. For example, common photo detector 306 and polarized photo detector 308 can each comprise one or more phototransistors, photoresistors and/or photodiodes that are sensitive to infrared light. The same or different types of sensor(s) of light can be included in each of common photo detector 306 and polarized photo detector 308. For example, the sensor of light in both common photo detector 306 and polarized photo detector 308 can be configured to generate an electrical (and/or other type of) signal in response to detecting one or more types of light. In such embodiments, for example, polarized photo detector 308 can include a dichroic analyzer and/or other type of filter(s), namely polarized filter 312, that blocks at least some types of polarized light from reaching its sensor of light. Polarized filter 312 can comprise Polaroid polarizing film that functions as a dichroic analyzer and is configured such that its axis of polarization is fixed orthogonal to the E-vector of the polarization of reflected light beam 210 when reflected light beam 210 is polarized as a result of reflecting off ribbon film 208 at its Brewster's angle. One skilled in the art would appreciate that, according to Malus' law, no light can pass though the filter when a filter's axes are orthogonal to the axes of light's polarization.

As a result, common photo detector 306 may be the only component of multi-element detector 204 that receives and determines the presence of reflected light beam 210 when reflected light beam 210 is polarized as a result of reflecting off ribbon film 208 at the proper Brewster's angle. In this regard, ribbon film 208 can be identified regardless of the properties (e.g., density, color, etc.) of ink layer 214 and without a snap plate. Hence a number of benefits may be realized by embodiments discussed herein, including cost benefits because a snap plate is currently more expensive than the cost of a polarized photo detector.

Further to that noted above, Brewster's Law from which Brewster's angle is derived, is applicable to transparent, translucent, and/or any other type of dielectric surface(s) that allow light to at least partially pass through. As a result, when ribbon film 208 comprises a reflective surface (as opposed to a transparent dielectric surface), reflected light beam 210 can be un-polarized and at least some light (e.g., portions of reflected light beam 210 that has axes other than that orthogonal to polarized filter 312) can pass through polarized filter 312 and be detected by the light sensor of polarized photo detector 308. In response to un-polarized light being detected by polarized filter 312, in some embodiments, an "un-polarized light detected signal" can be generated by polarized photo detector 308. The un-polarized light detected signal can indicate the presence of un-polarized light to other circuitry, such as a processor discussed in connection with FIG. 4. Similarly, at least a portion of reflected light beam 210 can be sensed simultaneously by common photo detector 306, which can be configured to generate a "ribbon detected signal" that indicates the presence of a ribbon in some embodiments. The un-polarized light detected signal, ribbon detected signal, and/or any other signals discussed herein can be any type of signal, including a common binary signal (e.g., a logical high digital 1 and/or logical low digital 0) and/or more complex signal (e.g., a signal that comprises a plurality of binary signals), among other things. Signals discussed herein can be transmitted via a wire, fiber, and/or any other signal carrying medium.

The circuitry that receives the un-polarized light detected signal and the ribbon detected signal can be included in multi-element detector 204 as shown in the example circuit diagram of FIG. 4. The circuitry shown in FIG. 4 is illustrated as being included in printer 100, but one or more of the components shown in FIG. 4 can be included in one or more other devices (such as laminating machines, facsimile machines, copy machines, packaging machines, etc.) and/or used for implementations in printing devices other than monitoring printer ribbon. For example, in addition to or instead of printer ribbon, embodiments discussed herein can be configured to analyze any suitable targeted substrate, such as for, e.g., detecting liner material, detecting retransfer material, detecting and/or monitoring remaining print media, detecting plastic cards and/or other printable substrates, detecting media that has been printed, locating a transponder inlay for encoding, identifying a component that is installed, etc. In some embodiments, to identify a component and/or other targeted substrate, a series of metallic strips and non-metallic strips may be used as a barcode (sometimes referred to herein as a "Brewster's Barcode") that can be read by detecting a series of un-polarized and polarized light over time, as discussed herein. Similarly, additional circuitry components may be included in printer 100 and/or one or more circuitry components shown in FIG. 4 may be omitted from some embodiments of printer 100.

Tri-state processor 402 may be included in multi-element detector 204 and be configured to determine, based on signals received from common photo detector 306 and/or polarized photo detector 308, whether there is a transparent surface made of a particular material (e.g., PET) or a reflective surface in the field of view of light beam 206. This determination may be made based upon, for example, determining that reflected light beam 210 is polarized (e.g., after reflecting off a transparent dielectric, such as PET) or un-polarized (e.g., after reflecting off a reflective surface, such as a metallic or mirrored surface).

Tri-state processor 402 may be further configured to determine, based on the type of material in the field of view of light beam 206, whether or not a printer ribbon needs replacement. For example, a data structure, such as data structure 500 shown in FIG. 5, can be used to determine whether or not a printer ribbon needs replacement. Data structure 500 can be stored in a non-transitory computer-readable storage device that is accessible by tri-state processor 402. Examples of non-transitory computer-readable storage devices are discussed below and may be included in tri-state processor 402 and/or any other aspect of embodiments discussed herein. Alternatively or additionally, tri-state processor 402 can include one or more logical gates and/or other hardware that causes tri-state processor 402 to be configured to execute a logical algorithm represented by data structure 500.

Columns 502 and 504 of FIG. 5 show the various states of signals that may be received from some embodiments of common photo detector 306 and polarized photo detector 308, respectively. For example, a "0" in column 502 represents common photo detector 306 is indicating the absence of light, and a "1" in column 502 represents common photo detector 306 is indicating the presence of light. Similarly, a "0" in column 504 represents polarized photo detector 308 is indicating the absence of un-polarized light, and a "1" in column 504 represents polarized photo detector 308 is indicating the presence of un-polarized light. (As noted above, light may become polarized after shining onto a particular type of surface at a particular angle, and then reflecting off the surface according to Brewster's Law.)

Column 506 of FIG. 5 shows example outputs and/or other types of determinations that may be made by tri-state processor 402 in accordance with some embodiments discussed herein, such as those consistent with that shown in FIG. 2A, that include multi-state detector 204 being configured to monitor the state of a printer ribbon that has colored (e.g., red, blue, green, yellow, etc.), black and/or other non-reflective ink for printing. The determinations of column 506 can be made regardless of the density of the ink on the ribbon and may be based on the material of the printer ribbon in combination with the angle of incidence of the light impacting the printer ribbon. For example, in response to determining that common photo detector 306 and polarized photo detector 308 generating a signal (e.g., logical low signal) indicating the absence of light, tri-state processor 402 can be configured to determine that there is no printer ribbon (and/or anything else that may reflect light) in the field of view of light emitter 202.

In response to determining that common photo detector 306 is indicating the absence of light and polarized photo detector 308 is detecting and indicating the presence of un-polarized light, tri-state processor 402 can be configured to determine that there is an error, because there should not be both an absence of any type of light and the presence of un-polarized light. In other words, in some embodiments common photo detector 306 can be configured to detect any type of light that polarized photo detector 308 can detect, hence polarized photo detector 308 detecting light that is not detected by common photo detector 306 can indicate that one or both photo detectors and/or other component discussed herein is experiencing an error and/or otherwise not functioning properly.

In response to determining that common photo detector 306 is indicating the presence of light and polarized photo detector 308 is indicating the absence of light, tri-state processor 402 can be configured to determine that there is printer ribbon, which may be used for printing black, colored and/or non-reflective ink onto a media, in the field of view of light emitter 202. As another example, in response to determining that common photo detector 306 and polarized photo detector 308 are indicating the presence of light, tri-state processor 402 can be configured to determine that there is a reflective surface, such as a metalized/metallic-based printer ribbon trailer, leader and/or other type of reflective surface, in the field of view of light emitter 202. The identifying of a printer ribbon trailer by tri-state processor 402 may cause systems in accordance with some embodiments discussed herein to determine, for example, that the printer ribbon needs to be replaced with a new printer ribbon. The identification of a printer ribbon leader by tri-state processor 402 may cause systems in accordance with some embodiments discussed herein to determine, for example, that the printer ribbon needs to be spooled forward before printing can take place.

Column 508 of FIG. 5 shows example outputs and/or other types of determinations that may be made by tri-state processor 402 in accordance with some embodiments discussed herein, such as those consistent with that shown in FIG. 2B, that include multi-state detector 204 being configured to monitor the state of a printer ribbon that has metallic ink for printing. For example, in response to determining that common photo detector 306 and polarized photo detector 308 are indicating the absence of light, tri-state processor 402 can be configured to determine an absence of printer ribbon (and/or any other surface that may reflect light) in the field of view of light emitter 202.

In response to determining that common photo detector 306 is indicating the absence of light and polarized photo detector 308 is indicating the presence of un-polarized light, tri-state processor 402 can be configured to determine that there is an error. In response to determining that common photo detector 306 is indicating the presence of light and polarized photo detector 308 is indicating the absence of light, tri-state processor 402 can be configured to determine that there is a transparent surface made of a material that causes polarized light to be reflected, such as a printer ribbon trailer and/or leader, in the field of view of light emitter 202. In this regard, for example, reflective metallic ink ribbons may include a transparent trailer and leader made of PET.

As another example, in response to determining that common photo detector 306 and polarized photo detector 308 are indicating the presence of light, tri-state processor 402 can be configured to determine that there is a reflective surface, such as that created by metallic ink that may be printed onto a media by printer 100, in the field of view of light emitter 202.

Column 510 of FIG. 5 shows example outputs and/or other types of determinations that may be made by tri-state processor 402 in accordance with some embodiments discussed herein, such as those consistent with that shown in FIG. 2C, that include multi-state detector 204 being configured to monitor the state of a printer ribbon that has a metallic ink for printing. The determinations of column 510 can be made based on the reflectivity of the ink on the ribbon and based on the material of the ribbon's leader/trailer in combination with the angle of incidence of the light impacting the printer ribbon's leader/trailer. For example, in response to determining that common photo detector 306 and polarized photo detector 308 are indicating the absence of light, tri-state processor 402 can be configured to determine that there is no reflective ink (and/or anything else that may reflect light) in the field of view of light emitter 202.

In response to determining that common photo detector 306 is indicating the absence of light and polarized photo detector 308 is indicating the presence of un-polarized light, tri-state processor 402 can be configured to determine that there is an error, because there should not be both an absence of any type of light and the presence of un-polarized light. In other words, in some embodiments common photo detector 306 can be configured to detect any type of light that polarized photo detector 308 can detect, hence polarized photo detector 308 indicating the presence of light that is not detected by common photo detector 306 can cause printer 100 to determine that one or both photo detectors and/or other component(s) are experiencing an error and/or otherwise not functioning properly.

In response to determining that common photo detector 306 is indicating the presence of light and polarized photo detector 308 is indicating the absence of light, tri-state processor 402 can be configured to determine that there a material that is non-reflective, which may be the ribbon's leader/trailer, in the field of view of light emitter 202. As another example, in response to determining that common photo detector 306 and polarized photo detector 308 are both indicating the presence of light, tri-state processor 402 can be configured to determine that there is a reflective surface, such as a metalized/metallic-based ink and/or other type of reflective surface, in the field of view of light emitter 202.

In some embodiments, as noted above, the indication of a printer ribbon trailer by tri-state processor 402 may cause systems in accordance with some embodiments discussed herein to determine, for example, that the printer ribbon needs to be replaced with a new printer ribbon. The indication of a printer ribbon leader by tri-state processor 402 may cause systems in accordance with some embodiments discussed herein to determine, for example, that the printer ribbon needs to be spooled forward before printing can take place.

In other embodiments, the presence and lack of un-polarized light can be used to store and convey machine-readable information similar to how black and white lines of a barcode are used to store and convey machine-readable information. For example, the media could include one or more reflective segments separated by one or more non-reflective segments, and then the media and/or tri-state sensor 128 may be moved relative to the reflective and non-reflective segments. When moving and functioning as described herein, tri-state sensor 128's polarized photo detector 308 may identify and generate a series of 1's and 0's, which maybe may be used to represent data that tri-state processor 402 (and/or any other component discussed herein) may be configured to interpret. Hence, some embodiments discussed herein may be used to implement a new type of barcode, sometimes referred to herein as a Brewster's Barcode, which is based on a series of material segments arranged next to each other that cause reflected light to be polarized or un-polarized. The Brewster's Barcode can be used for any suitable purpose including, for example, article identification (e.g., make and manufacturer of the ribbon, ribbon color, ribbon length, etc.), article authentication (which may be used to, e.g., confirm that the ribbon is authorized for use in the printer), among other things.

In some embodiments (not shown), tri-state processor 402 may be omitted from printer 100 and, for example, processor 404 and/or any other component can be configured to perform the functionality discussed herein in reference to tri-state state processor 402. In other embodiments, tri-state state processor 402, processor 404 and/or any other component(s) can be configured to perform the functionality discussed herein in reference to tri-state state processor 402.

Processor 404 and/or tri-state processor 402 can, for example, each or collectively be embodied as various means including one or more microprocessors with accompanying digital signal processor(s), processor(s) without an accompanying digital signal processor, one or more coprocessors, multi-core processors, controllers, computers, various other processing elements including integrated circuits such as, for example, an ASIC (application specific integrated circuit) or FPGA (field programmable gate array), or some combination thereof. Accordingly, although each is shown in FIG. 4 as a separate, single processor, in some embodiments the processor 404 and/or tri-state processor 402 comprises a plurality of processors and/or any other type of control circuitry. The plurality of processors, for example, may be embodied on a single computing device or may be distributed across a plurality of computing devices collectively configured to function as processor 404 and/or tri-state processor 402. The plurality of processors may be in operative communication with each other and may be collectively configured to perform one or more functionalities of processor 404 and/or tri-state processor 402 as described herein.

In an example embodiment, processor 404 and/or tri-state processor 402 is configured to execute instructions stored in memory 406 (discussed below) and/or that are otherwise accessible to processor 404 and/or tri-state processor 402. These instructions, when executed by processor 404 and/or tri-state processor 402, may cause printer 100 to perform one or more of the functionalities described herein. As such, whether configured by hardware, firmware/software methods, or by a combination thereof, processor 404 and/or tri-state processor 402 may comprise an entity capable of performing operations according to embodiments of the present invention while configured accordingly. Thus, for example, when processor 404 and/or tri-state processor 402 is embodied as an ASIC, FPGA or the like, processor 404 and/or tri-state processor 402 may comprise specifically configured hardware for conducting one or more operations described herein. Alternatively, as another example, when processor 404 and/or tri-state processor 402 is embodied as an executor of instructions, such as those that may be stored in memory 406, the instructions may specifically configure processor 404 and/or tri-state processor 402 to perform one or more algorithms and operations described herein.

Processor 404 may be configured to receive a signal from input/output module 408, which may include specialized circuitry, one or more ports (parallel ports, serial ports, such as universal serial bus, "USB," ports, and/or any other ports), and/or any other component that facilitates the reception of signals from an input component. In some embodiments, input/output module 408 can function as a user input interface and, in turn, receive data from any of a number and/or types of devices and/or users (e.g., local user, network user, etc.). For example, input/output module 408 may be electrically coupled to a touch-screen display component and/or other type of a user input device (e.g., keypads, mouse, etc.). Input/output module 408 can also be configured to function as an output module that provides data to, e.g., a speaker and/or other output device. Although more than one input/output module can be included in printer 100, only one is shown in FIG. 4 (like the other components discussed herein) to avoid overcomplicating the drawing. Similarly, input/output module 408 can be divided into separate input module(s) and output module(s).

Processor 404 can also be configured to utilize communications module 410 to communicate with one or more remote machines (e.g., via a network). Communications module 410 can include hardware, software, and/or any other means for transmitting and/or receiving data, content or any other type of information from a network or other type of device.

In some embodiments, processor 404 and/or tri-state processor 402 is in communication with and/or includes a non-transitory storage device, such as memory 406, which may be volatile and/or non-volatile memory that stores content, data and/or any other information. For example, memory 406 can store information generated by, transmitted from, and/or received by, printer 100. Also for example, memory 406 typically stores software applications, instructions or the like for processor 404 and/or tri-state processor 402 to perform steps associated with operation of printer 100. For example, memory 406 may be a non-transitory storage medium that stores computer program code comprising instructions or other executable portions that processor 404 and/or tri-state processor 402 executes to perform the functions described above and below with regard to, e.g., FIGS. 6-8.

In this regard, printer 100 may include any type of circuitry to facilitate the functionality discussed herein. Additionally, embodiments discussed herein are not limited to printers and may be used to in apparatuses and systems that do not include printing functionality. For example, circuitry commonly found in various computing devices and other types of machines (e.g., desktop computer, laptop computer, tablet, etc.) may be configured to perform at least some of the functionality discussed herein.

Figure 6:
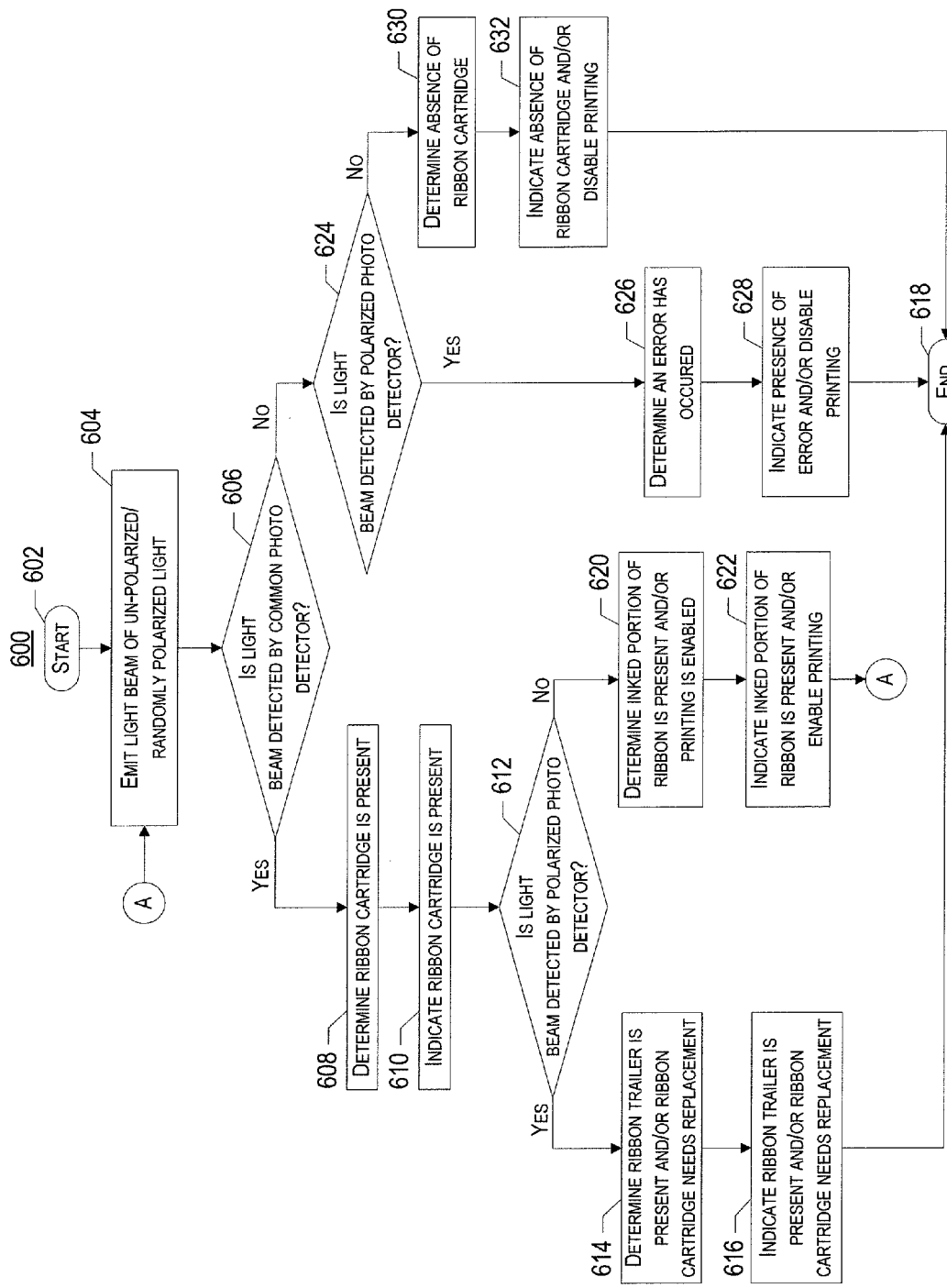
FIGS. 6-8 show flow diagrams of example machine-implemented methods in accordance with some embodiments discussed herein.
Figure 7:
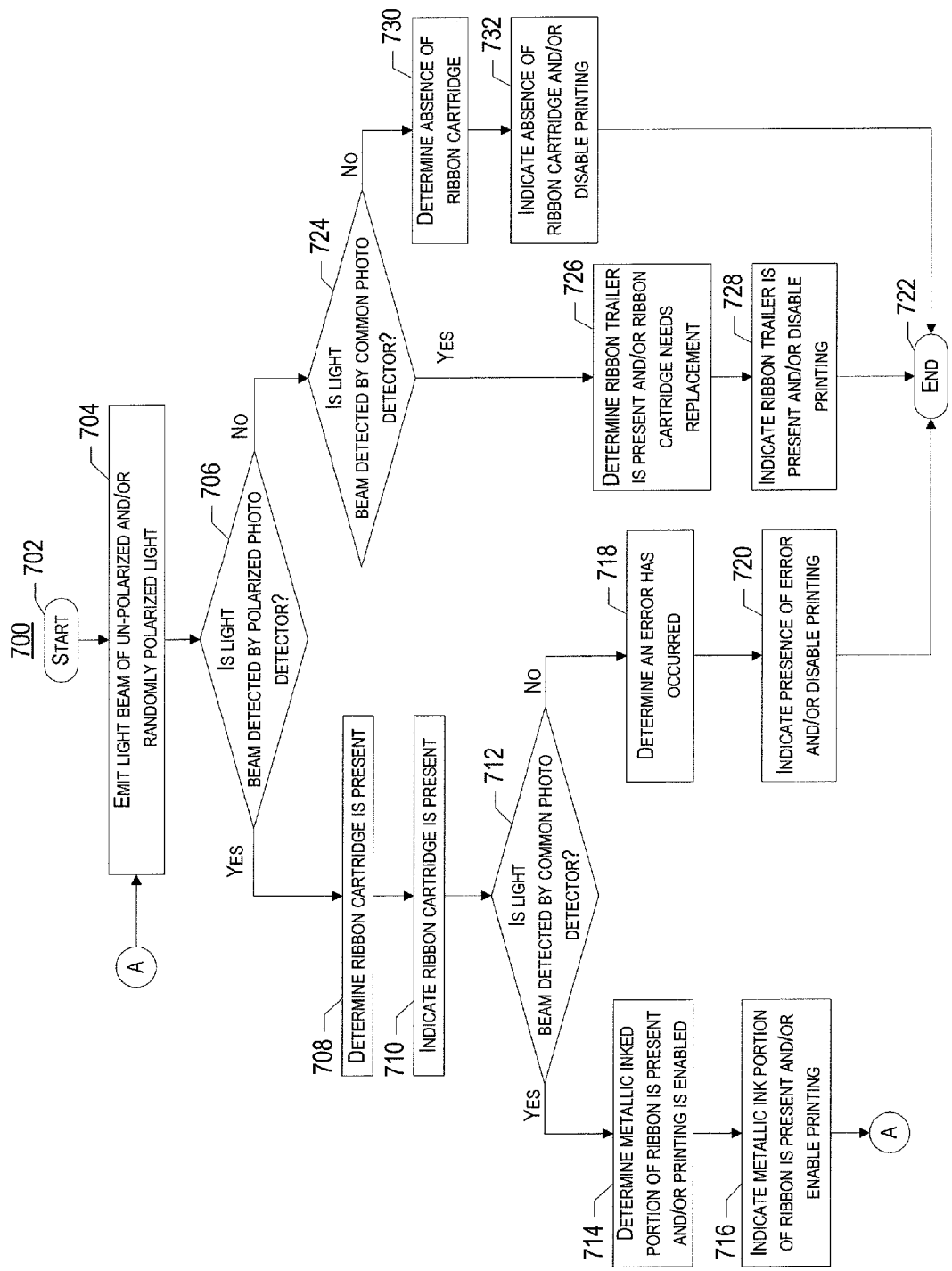
Figure 8:
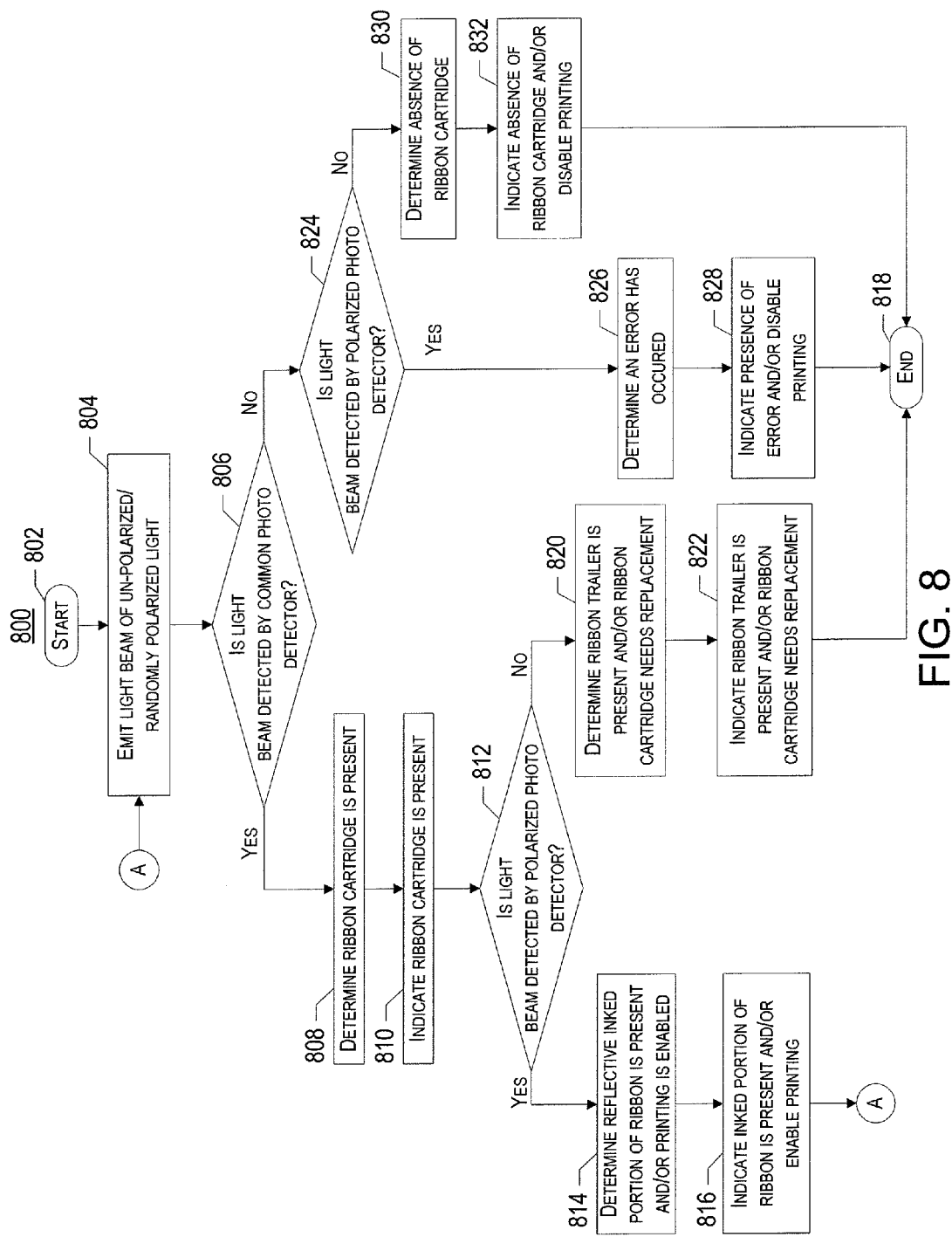

FIG. 6 shows process 600, FIG. 7 shows process 700 and FIG. 8 shows process 800. Processes 600, 700 and 800 are each represented by a flow diagram in accordance with some exemplary methods, computer program products and/or systems discussed herein. It will be understood that each operation, action, step and/or other types of functions shown in the diagrams, and/or combinations of functions in the diagrams, can be implemented by various means. Means for implementing the functions of the flow diagrams, combinations of the actions in the diagrams, and/or other functionality of example embodiments of the present invention described herein, may include hardware and/or a computer program product including a computer-readable storage medium (as opposed to or in addition to a computer-readable transmission medium) having one or more computer program code instructions, program instructions, or executable computer-readable program code instructions stored therein. For example, program code instructions associated with FIGS. 6-8 may be stored on one or more storage devices, such as memory 406, and executed by one or more processors, such as processor 404 and/or tri-state processor 402. Additionally or alternatively, one or more of the program code instructions discussed herein may be stored and/or performed by distributed components, such as those that may be connected to printer 100 via a network or other communications interface (such as communications module 410). As will be appreciated, any such program code instructions may be loaded onto computers, processors, other programmable apparatuses or network thereof from one or more computer-readable storage mediums to produce a particular machine, such that the particular machine becomes a means for implementing the functions of the actions discussed in connection with, e.g., FIGS. 6-8 and/or the other drawings discussed herein.

The program code instructions stored on the programmable apparatus may also be stored in a non-transitory computer-readable storage medium that can direct a computer, a processor (such as processor 404 and/or tri-state processor 402) and/or other programmable apparatus to function in a particular manner to thereby generate a particular article of manufacture. The article of manufacture becomes a means for implementing the functions of the actions discussed in connection with, e.g., FIGS. 6-8. The program code instructions may be retrieved from a computer-readable storage medium and loaded into a computer, processor, or other programmable apparatus to configure the computer, processor, or other programmable apparatus to execute actions to be performed on or by the computer, processor, or other programmable apparatus. Retrieval, loading, and execution of the program code instructions may be performed sequentially such that one instruction is retrieved, loaded, and executed at a time. In some example embodiments, retrieval, loading and/or execution may be performed in parallel by one or more machines, such that multiple instructions are retrieved, loaded, and/or executed together. Execution of the program code instructions may produce a computer-implemented process such that the instructions executed by the computer, processor, other programmable apparatus, or network thereof provide actions for implementing the functions specified in the actions discussed in connection with, e.g., processes 600, 700 and 800.

Process 600, which may be executed, partially or wholly, in accordance with some embodiments discussed herein, such as those in accordance with FIG. 2A, that are configured to identify colored and/or black ink ribbons having a reflective trailer/leader portion. Process 600 starts at 602 and at 604 a light beam (e.g., light beam 206) can be emitted from a light emitter (e.g., light emitter 202). Further to the above discussion, the light beam can comprise un-polarized light and/or randomly polarized light (which may be interpreted by some embodiments as un-polarized light).

At 606, a determination can be made whether a light beam is detected by a common photo detector (e.g., common photo detector 306). For example, processor 404 may receive one or more signals from tri-state processor 402 and/or common photo detector 306, which are used by processor 404 to make the determination at 606. In some embodiments, like other functionality discussed herein, tri-state processor 402 can be configured to make the determination at 606.

In response to determining at 606 that a light beam has been and/or is being identified by outputs of the common photo detector, a determination can be made at 608 that a ribbon cartridge (and/or any other type of component) is present and/or otherwise loaded into a printer (and/or any other type of component). In some embodiments, the processor and/or other component can be configured to indicate at 610 to a user and/or remote system (using, e.g., input/output module 408 and/or communications module 410) that a ribbon cartridge is present. For example, at 610, a light emitting device may be illuminated, a ribbon cartridge present icon may be displayed, a ribbon cartridge needed icon may be removed from a display, etc.

At 612, a determination can be made by a processor as to whether or not a light beam is or has been detected by a polarized photo detector (e.g., polarized photo detector 308). For example, processor 404 may receive one or more signals from tri-state processor 402 and/or polarized photo detector 308, which are used by processor 404 to make the determination at 612. In some embodiments, 612 and 606 can be executed simultaneously, near-simultaneously and/or in reverse order.

In response to determining at 612 that an un-polarized light beam has been and/or is being detected by the polarized photo detector, a determination can be made at 614 that a ribbon trailer is in the field of view of the multi-state detector and/or that the ribbon cartridge is "out" and needs replacing. In some embodiments, a more general determination can be made at 614, such that any reflective surface (e.g., metallic ink, for example) is in the field of view of the multi-state detector at that time.

At 616, the processor and/or other component can be configured to convey to a user and/or to a remote system (using, e.g., input/output module 408 and/or communications module 410) information associated with the determination made at 614. For example, at 616, a light emitting device may be illuminated, a ribbon trailer icon may be displayed, a warning message to replace a ribbon may be sent to a computer or other type of administrator, etc. Process 600 may then end at 618. As another example, the presence of a reflective surface can represent anything else (e.g., a bit of data that is part of Brewster's code) and be interpreted by a system accordingly.

In some embodiments, one or more additional steps may be included in process 600. For example, one or more steps may be included before 614 that enable the printer and/or other machine to determine whether the reflective portion is a ribbon leader (rather than a ribbon trailer). For example, the system may be configured to determine how far the ribbon has been advanced since being installed and use this information to determine whether the reflective portion is a new ribbon's leader or an old ribbon's trailer. If a determination is made that the reflective portion is a ribbon leader, the machine may be configured to spool the ribbon forward for printing while executing step 604 and the other steps of process 600.

Returning to 612, in response to determining (based on output signals provided by the polarized photo detector) that an un-polarized light beam has not been detected and/or an indication that un-polarized light is absent, a determination can be made at 620 that an inked portion of the ribbon is present in the field of view of the multi-state detector and/or that printing is enabled. The determination of a non-reflective surface may represent a bit of data that may be included in a data set encoded as a Brewster's barcode.

At 622, the processor and/or other component can be configured to convey to a user and/or to a remote system (using, e.g., input/output module 408 and/or communications module 410) information associated with the determination made at 620. For example, at 622, a light emitting device may be illuminated, a printer-ready icon may be displayed, an enabled for printing message/status indicator may be sent to a computer or other type of administrator, etc. Process 600 may then proceed to 604 and continue to monitor the ribbon, reading the Brewster's barcode, and/or performing any other suitable function by emitting an un-polarized beam of light and executing the steps of process 600.

Returning to 606, in response to determining (using the common photo detector) that a light beam has not been detected and/or there is an indication of an absence of the type of light emitted at 604 (e.g., absence of light in a particular wavelength, having pulse frequency, etc.), a determination can be made at 624 as to whether or not the polarized photo detector has detected or is detecting un-polarized light of the type emitted at 604.

In response to determining at 624 that the polarized photo detector is detecting and indicating the presence of un-polarized light, despite the common photo detector indicating an absence of light, a determination can be made by the system at 626 that an error has occurred. The presence of the error can be conveyed to a user and/or other system at 628. For example, at 628, a light emitting device may be illuminated, a ribbon detector error icon may be displayed, etc. Process 600 may then end at 618.

In response to determining at 624 that the polarized photo detector is indicating the absence of un-polarized light, a determination can be made by the system at 630 that there is no ribbon cartridge installed in the printer. The absence of the ribbon cartridge can then be conveyed to a user and/or other system at 632. For example, at 632, a light emitting device may be illuminated, a missing printer cartridge icon may be displayed, a printer cartridge installed icon may be removed from a display, etc. Process 600 may then end at 618.

FIG. 7 shows process 700, which may be executed, partially or wholly, in accordance with some embodiments discussed herein, such as those in accordance with FIG. 2B that are configured to identify reflective metallic ribbons having a clear trailer/leader portion. Process 700 starts at 702 and at 704 a light beam (e.g., light beam 206) can be emitted from a light emitter (e.g., light emitter 202). Further to the above discussion, the light beam can comprise un-polarized and/or randomly polarized light.

At 706, a determination can be made whether a light beam is detected by a polarized photo detector (e.g., polarized photo detector 308). For example, processor 404 may receive one or more signals from tri-state processor 402 and/or polarized photo detector 308, which are used by processor 404 to make the determination at 706. In some embodiments, like other functionality discussed herein, tri-state processor 402 can be configured to make the determination at 706.

In response to determining at 706 that a light beam has been and/or is being detected by the polarized photo detector, a determination can be made at 708 that a ribbon cartridge (and/or any other type of component) is present and/or otherwise loaded into a printer (and/or any other type of component). In some embodiments, the processor and/or other component can be configured to indicate at 710 to a user and/or remote system (using, e.g., input/output module 408 and/or communications module 410) that a ribbon cartridge is present. For example, at 710, a light emitting device may be illuminated, a ribbon cartridge present icon may be displayed, a ribbon cartridge needed icon may be removed from a display, etc.

At 712, a determination can be made by a processor as to whether or not a light beam is or has been detected by a common photo detector (e.g., common photo detector 306). For example, processor 404 may receive one or more signals from tri-state processor 402 and/or common photo detector 306, which are used by processor 404 to make the determination at 712. In some embodiments, 712 and 706 can be executed simultaneously, near-simultaneously and/or in reverse order.

In response to determining at 712 that a light beam has been and/or is being detected by the common photo detector, a determination can be made at 714 that a metallic inked portion of ribbon is present in the field of view of the multi-state detector and/or that printing is enabled. For example, a circuit board, radio frequency identification (RFID) antenna, any other type of antenna, and/or any other component that can be created using printing technology may be printed using metallic ink based on the determination at 714.

At 716, the processor and/or other component can be configured to convey to a user and/or to a remote system (using, e.g., input/output module 408 and/or communications module 410) information associated with the determination made at 714. For example, at 716, a light emitting device may be illuminated, a printer-ready icon may be displayed, an enabled for printing message/status indicator may be sent to a computer or other type of administrator, etc. Process 700 may then proceed to 704 and continue to monitor the ribbon by emitting an un-polarized beam of light and executing the steps of process 700.

Returning to 712, in response to determining (based on output signals provided by the common photo detector) that a light beam of the type emitted at 704 has not been detected and/or is absent, despite the polarized photo detector detecting and indicating the presence of un-polarized light of the type emitted at 704, a determination can be made by the system at 718 that an error has occurred. The presence of the error can be conveyed to a user and/or other system at 720. For example, at 720, a light emitting device may be illuminated, a ribbon detector error icon may be displayed, etc. Process 700 may then end at 722.

Returning to 706, in response to determining (using the polarized photo detector) that a light beam has not been detected and/or there is an indication of the absence of the type of light emitted at 704 (e.g., absence of un-polarized light in a particular wavelength, having a predetermined pulse frequency, etc.), a determination can be made at 724 as to whether or not the common photo detector has detected or is detecting light of the type emitted at 704.

In response to determining at 724 that the common photo detector is detecting and indicating the presence of the type of light emitted at 704, a determination can be made at 726 that a transparent ribbon trailer is in the field of view of the multi-state detector and/or that the ribbon cartridge is "out" and needs replacing.

At 728, the processor and/or other component can be configured to convey to a user and/or to a remote system (using, e.g., input/output module 408 and/or communications module 410) information associated with the determination made at 726. For example, at 728, a light emitting device may be illuminated, a ribbon trailer icon may be displayed, a warning message to replace a ribbon may be sent to a computer or other type of administrator, etc. Process 700 may then end at 722.

In some embodiments, one or more additional steps may be included in process 700. For example, one or more steps may be included after 724 and before 726 that enable the printer and/or other machine to determine whether the transparent portion is a ribbon leader (rather than a ribbon trailer). For example, the system may be configured to determine how far the ribbon has been advanced since being installed and use this information to determine whether the transparent portion is a new ribbon's leader or an old ribbon's trailer. If a determination is made that the transparent portion is a ribbon leader, the machine may be configured to spool the ribbon forward for printing and execute step 704 and the other steps of process 700 to determine when the metallic ink is present in the detector's field of view.

Returning to 724, in response to determining that the common photo detector is not detecting and/or indicating the presence of the type of light emitted at 704, a determination can be made at 730 that there is no metallic ribbon cartridge installed in the printer. The absence of the ribbon cartridge can then be conveyed to a user and/or other system at 732. For example, at 732, a light emitting device may be illuminated, a missing printer cartridge icon may be displayed, a printer cartridge installed icon may be removed from a display, etc. Process 700 may then end at 722.

Process 800, which may be executed, partially or wholly, in accordance with some embodiments discussed herein, such as those in accordance with FIG. 2C, that are configured to identify reflective ink ribbons having a non-reflective trailer/leader portion. Process 800 starts at 802 and at 804 a light beam (e.g., light beam 206) can be emitted from a light emitter (e.g., light emitter 202). Further to the above discussion, the light beam can comprise un-polarized light and/or randomly polarized light (which may be interpreted by some embodiments as un-polarized light).

At 806, a determination can be made whether a light beam is detected by a common photo detector (e.g., common photo detector 306). For example, processor 404 may receive one or more signals from tri-state processor 402 and/or common photo detector 306, which are used by processor 404 to make the determination at 806. In some embodiments, like other functionality discussed herein, tri-state processor 402 can be configured to make the determination at 806.

In response to determining at 806 that a light beam has been and/or is being identified by outputs of the common photo detector, a determination can be made at 808 that a ribbon cartridge (and/or any other type of component) is present and/or otherwise loaded into a printer (and/or any other type of component). In some embodiments, the processor and/or other component can be configured to indicate at 810 to a user and/or remote system (using, e.g., input/output module 408 and/or communications module 410) that a ribbon cartridge is present. For example, at 810, a light emitting device may be illuminated, a ribbon cartridge present icon may be displayed, a ribbon cartridge needed icon may be removed from a display, etc.

At 812, a determination can be made by a processor as to whether or not a light beam is or has been detected by a polarized photo detector (e.g., polarized photo detector 308). For example, processor 404 may receive one or more signals from tri-state processor 402 and/or polarized photo detector 308, which are used by processor 404 to make the determination at 812. In some embodiments, 812 and 806 can be executed simultaneously, near-simultaneously and/or in reverse order.

In response to determining at 812 that an un-polarized light beam has been and/or is being detected by the polarized photo detector, a determination can be made at 814 that a surface having reflective ink is in the field of view of the multi-state detector and/or that the printer is enabled to print.

At 816, the processor and/or other component can be configured to convey to a user and/or to a remote system (using, e.g., input/output module 408 and/or communications module 410) information associated with the determination made at 814. For example, at 816, a light emitting device may be illuminated, a printer-ready icon may be displayed, an enabled for printing message/status indicator may be sent to a computer or other type of administrator, etc. Process 800 may then proceed to 804 and continue to monitor the ribbon, reading the Brewster's barcode, and/or performing any other suitable function by emitting an un-polarized beam of light and executing the steps of process 800.

Returning to 812, in response to receiving (based on output signals provided by the polarized photo detector) an indication that un-polarized light is absent (e.g., only polarized light has been detected), a determination can be made at 820 that a non-reflective surface (e.g., ribbon trailer/leader, etc.) is in the field of view of the multi-state detector at that time. As another example, the presence of a non-reflective surface can represent anything else (e.g., a bit of data that is part of Brewster's code) and be interpreted by a system accordingly.

At 822, the processor and/or other component can be configured to convey to a user and/or to a remote system (using, e.g., input/output module 408 and/or communications module 410) information associated with the determination made at 820. For example, at 822, a light emitting device may be illuminated, a ribbon trailer icon may be displayed, a warning message to replace a ribbon may be sent to a computer or other type of administrator, etc. Process 800 may then end at 818.

In some embodiments, one or more additional steps may be included in process 800. For example, one or more steps may be included before 820 and/or after 812 that enable the printer and/or other machine to determine whether the non-reflective portion is a ribbon leader (rather than a ribbon trailer). For example, the system may be configured to counter motor steps since the ribbon was installed determine how far the ribbon has been advanced since being installed, and use this information to determine whether the reflective portion is a new ribbon's leader or a used ribbon's trailer. If a determination is made that the non-reflective portion is a ribbon leader, the machine may be configured to return to 804 (instead of ending at 818) and spool the ribbon forward for printing while executing the other steps of process 800.

Returning to 806, in response to determining (using the common photo detector) that a light beam has not been detected and/or there is an indication of an absence of the type of light emitted at 804 (e.g., absence of light in a particular wavelength, having pulse frequency, etc.), a determination can be made at 824 as to whether or not the polarized photo detector has detected or is detecting un-polarized light of the type emitted at 804.

In response to determining at 824 that the polarized photo detector is detecting and indicating the presence of un-polarized light, despite the common photo detector indicating an absence of light, a determination can be made by the system at 826 that an error has occurred. The presence of the error can be conveyed to a user and/or other system at 828. For example, at 828, a light emitting device may be illuminated, a ribbon detector error icon may be displayed, etc. Process 800 may then end at 818.

In response to determining at 824 that the polarized photo detector is indicating the absence of un-polarized light, a determination can be made by the system at 830 that there is no ribbon cartridge installed in the printer. The absence of the ribbon cartridge can then be conveyed to a user and/or other system at 832. For example, at 832, a light emitting device may be illuminated, a missing printer cartridge icon may be displayed, a printer cartridge installed icon may be removed from a display, etc. Process 800 may then end at 818.

There are practical issues to consider in the design and function of a detector circuit that employs sensors performing measurements on physical systems. One of these considerations is noise in the detector circuits. Systemic noise (that which is emitted by other electronic components and is coupled throughout the system) must be addressed in generally familiar ways (that is, filtering, isolation, proper grounding, etc.). However, detector noise can also emanate from the physical structure that is being monitored. In the case of the detector described herein, a significant source of detector noise can be the ribbon film itself.

Figure 9:
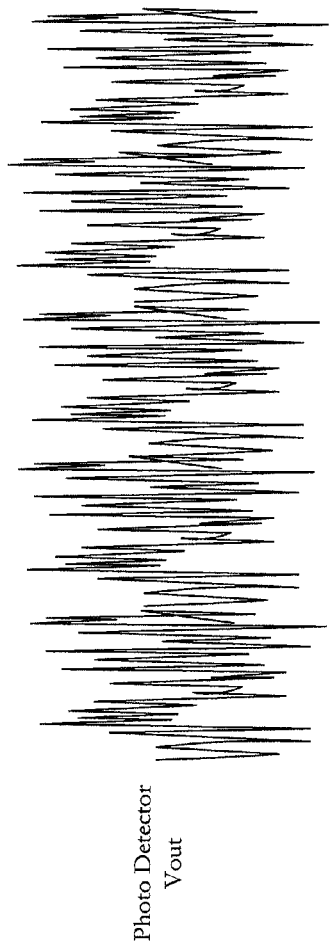
FIG. 9 is a schematic representation of noise in the photo detector output.

Referring back to FIG. 1 it can be seen that the web 126 (or the ribbon film 208) travels a path through the printer device 110, passing under the tri-state detector 128 along the way. Recall that the light emitter must maintain an angle α, Brewster's angle, at the surface of the film 208 to polarize some of the light reflected into the detector 204. In the depicted configuration, the surface of the film 208 exhibits vibration, or "ripples," as it moves through the printer. The result is illustrated in FIG. 9.

When the detectors (both the common photo detector 306 and the polarized detector 308 (FIG. 3A)) produce an output signal proportional to the light intensity that reaches them, the ripple of the ribbon film surface can produce output fluctuations. FIG. 9 illustrates an example of the output of one of the detectors when the film surface exhibits ripple as the film passes through the printer. When the surface of the ribbon film vibrates, light reflected from the surface is scattered at diverging angles rather than being reflected at the desired angle. This may result in an erratic detector output as illustrated in FIG. 9. If this erratic signal fluctuates around the detector threshold for a "true" ("1") or "false" ("0") output, then the detector may be rendered useless.

Figure 10:
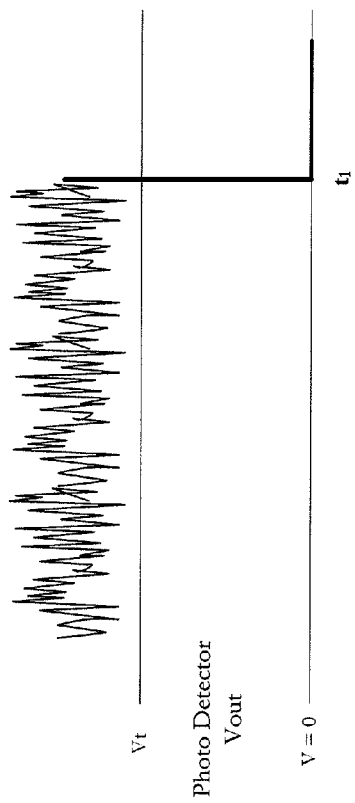
FIG. 10 is a graphical representation of an output voltage signal from the photo detector.

Referring to FIG. 10, there is shown an optimal detector circuit output. The threshold of positive detection (that is, an output indication that a ribbon film is present in the printer) is shown as Vt, the threshold voltage level. When the photo detector output (either one) exceeds the threshold Vt, the detector output goes to "1", as in FIG. 5, indicating a positive result for one of the photo detectors. When the ribbon film runs out, or is broken, as indicated at $t_1$ in FIG. 10, the output drops to zero, the "no ribbon" condition in FIG. 5. It is important that the fluctuations ("noise") in the detector output be kept from crossing the detector threshold Vt and creating false positives or negatives.

There are several potential solutions to this problem. Of course, filtering the output signal is one option, but it usually comes at a cost of responsiveness. Filtering the output signal introduces some delay in the response time of the detector, which may be detrimental to the detector function if fast response is important. If the printer can be damaged by running operational print cycles after the ribbon film runs out, then fast response is important.

Another potential solution resides in the signal level of the detector output. It may be possible to boost the output level to a point where all of the circuit noise is pushed above the detection threshold level, as shown in FIG. 10. This may be accomplished by adjusting the gain of the detector output to a point where the noise does not affect the detector function. This assumes that the noise level is not so high that there is little room below Vt for establishing a reliable detection level.

Another approach may be scaling the detector output. Rather than operating at nominal digital levels (between 0 and 5 volts) where noise can degrade a large portion of the detector range, the detector output might be scaled to operate from 0 to 10 or 15 volts whereby the circuit noise band may be limited to a smaller segment of the operating level. It may be possible to set a reliable detection threshold below the noise band in the output signal.

Figure 11:
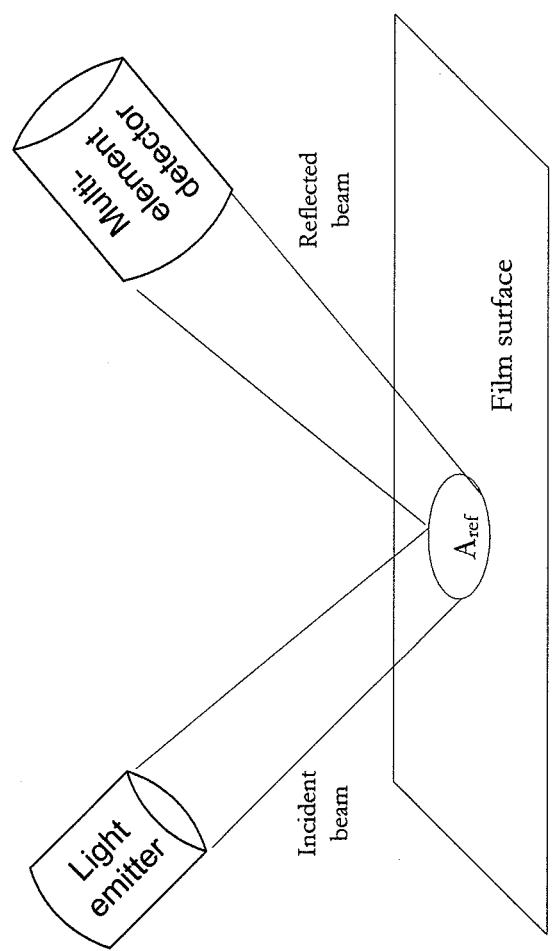
FIG. 11 is a schematic drawing of emitted light striking a film surface and reflecting to the photo detector.

It may also be possible to use the light source to reduce the effect of a rippling ribbon film. Rather than employing a narrow light beam, which is by nature highly susceptible to scattering off a vibrating surface (i.e., the rippling ribbon), it may be possible to reduce the overall noise level by spreading a broader light beam onto the film surface. See FIG. 11. If the detector was configured to receive light reflected from a larger area ($A_{ref}$) of the ribbon film surface, the overall effect of small oscillations in the surface of the film would be reduced. More light would be gathered into the photo detectors and the noise band in the detector output would be more manageable. This likely would require a broader beam of light emitted from the light emitter 202 (FIG. 2) of the detector, which could be achieved with a different emitter or perhaps by lensing the output of the emitter to spread the emitted light.

A corollary approach may be employing an array of photo detectors rather than just one. Because the scattered reflected light beam would contain components that would "miss" the primary detector, a group of detectors arranged in a pattern around the primary detector would likely collect more of the light scattered by the rippling ribbon surface. Because the Brewster's angle has a five degree window for polarization, a small array of detectors offers the possibility to capture both unpolarized and polarized light reflected off the ribbon film.

Finally, it may be possible to make physical adjustments to the printer device to damp the vibrations causing the surface of the film to ripple. The film might be passed through rollers immediately before and after the detector. It might pass over a backing plate at the point of detection to stabilize the film surface, although a small hole might be necessary in such a plate at the exact point where the detector's light beam is aimed and reflected. That would permit the light beam to pass unreflected when the film runs out so that a "film out" indication would still be produced by the detector.

It may be necessary to employ a combination of these techniques to overcome surface ripple in the medium (here, ribbon film) being monitored by the detector. Perhaps a small initial filter combined with output scaling would reduce the noise band to a manageable portion of the detection band so that erratic results can be avoided without slowing the circuit performance to unacceptable speed. Other combinations of techniques may be used successfully.

Many modifications and other embodiments of the inventions set forth herein will come to mind to one skilled in the art to which these inventions pertain having the benefit of the teachings presented in the foregoing descriptions and the associated drawings. For example, a plurality of multi-state detectors can be used simultaneously and/or combined into a single system. In such embodiments, each of the multi-state detectors may be configured to emit various types of light beams relative to the others and detect polarized and un-polarized versions of the expected light beams (e.g., each light beams having a different wavelength and/or pulse patterns). For example, a first multi-state sensor can be configured to analyze polarized v. un-polarized infrared light to determine the presence of in printer ribbon, while a second multi-state sensor can be configured to analyze colored stripes and/or other patterns (e.g., using a blue-colored light emitter and receives configured to include a color filter as well). The colored stripes may be used to determine, for example, relative positioning, type of ribbon, and/or other information. Additionally, rather than or in addition to stripes, two-dimensional codes, multi-color codes, multi-material codes (e.g., stripes of PET and reflective materials) and/or other types markings can be read, analyzed and interpreted using various embodiments discussed herein.

Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method, comprising:
   emitting light into a field of view;
   indicating whether the light is present in the field of view by signals from a multi-element detector; and
   indicating whether at least a portion of the light is polarized by a signal from the multi-element detector;
   wherein emitting the light comprises shining the light onto a printer ribbon such that the light's angle of incidence is within 5 degrees of Brewster's angle associated with the printer ribbon's material.

2. The method of claim 1, wherein indicating whether the light is present comprises generating a common light signal indicating that the light was detected by the multi- element detector.

3. The method of claim 1, wherein indicating at least a portion of the light is polarized comprises generating a polarized light signal.

4. The method of claim 1 further comprising in response to receiving, by a processor, indications whether the light is present and whether the light is polarized, determining whether an inked portion of a printer ribbon is in the field of view.

5. The method of claim 1 further comprising using a polarizing filter to determine whether the light is polarized.

6. The method of claim 5, wherein using the polarizing filter comprises using a dichroic analyzer film.

7. The method of claim 1, wherein emitting the light into the field of view comprises emitting infrared light.

8. The method of claim 1 further comprising providing a cylindrical housing surrounding light sensors, the cylindrical housing configured to reduce optical noise received by the light sensors.

9. The method of claim 1 further comprising outputting data to a processor of a printer representative of whether the light is present and whether the light is polarized.

10. The method of claim 9, further comprising:
reducing noise effects in the light detectors caused by rippling on the surface of a printer ribbon by electronic adjustment of the detector signals.

11. The method of claim 10 wherein,
the electronic adjustment is one or more of detector gain adjustment or detector signal scaling.

12. The method of claim 9, further comprising:
reducing noise effects in the light detectors caused by rippling on the surface of a printer ribbon by spreading the incident light over a greater area of the surface of the ribbon.

13. The method of claim 9 further comprising:
reducing noise effects in the light detectors caused by rippling on the surface of a printer ribbon by employing an array of multi-element light detectors.

14. The method of claim 9 further comprising:
reducing noise effects in the light detectors caused by rippling on the surface of a printer ribbon by adding physical damping features to the printer ribbon path.

15. A method, comprising:
emitting light into a field of view;
indicating whether the light is present in the field of view by signals form a multi-element detector;
indicating whether at least a portion of the light is polarized by a signal from the multi-element detector; and
in response to receiving, by a processor, indications whether the light is present and whether the light is polarized, determining whether an inked portion of a printer ribbon is in the field of view.

16. A new method comprising:
emitting light into a field view;
indicating whether the light is present in the field of view by signals from a multi-element detector;
indicating whether at least a portion of the light is polarized by a signal from the multi-element detector;
outputting data to a processor of a printer representative of whether the light is present and whether the light is polarized; and
reducing noise effects in the light detectors caused by rippling on a surface of a printer ribbon by at least one of: electronic adjustment of the detector signals, spreading the incident light over a greater area of the surface of the ribbon, employing an array of multi-element light detectors, or adding physical damping features to a printer ribbon path.

* * * * *